(12) United States Patent
Bunel et al.

(10) Patent No.: US 6,399,534 B2
(45) Date of Patent: Jun. 4, 2002

(54) BIDENTATE ORGANIC PHOSPHITE LIGANDS AND COMPOSITIONS

(75) Inventors: Emilio E. Bunel, Wilmington, DE (US); Helen S. M. Lu, Wallingford, PA (US); Kenneth Gene Moloy, Newark, DE (US); Shawn H. Phillips, Lancaster, CA (US); Kathryn E. Schwiebert, Wilmington, DE (US); Wilson Tam, Boothwyn; Nora Radu, Landenburg, both of PA (US)

(73) Assignee: E. I. du Pont de Nemours and Company, Wilmington (DE)

( * ) Notice: Subject to any disclaimer, the term of this patent is extended or adjusted under 35 U.S.C. 154(b) by 0 days.

(21) Appl. No.: 09/916,129

(22) Filed: Jul. 26, 2001

Related U.S. Application Data

(62) Division of application No. 09/399,252, filed on Sep. 20, 1999.

(51) Int. Cl.$^7$ .............................................. B01J 31/18
(52) U.S. Cl. ........................... 502/155; 568/6; 568/454; 502/162; 556/16; 556/136
(58) Field of Search ..................... 568/8, 454; 502/155, 502/162; 556/16, 136

(56) References Cited

U.S. PATENT DOCUMENTS 5,874,641 A * 2/1999 Burke et al. ................ 568/454
5,952,530 A * 9/1999 Argyropoulos et al. ..... 568/454

* cited by examiner

Primary Examiner—Sreeni Padmanabhan

(57) ABSTRACT

This invention relates to multidentate organic phosphite ligands and their compositions with Group VIII metals.

10 Claims, No Drawings

BIDENTATE ORGANIC PHOSPHITE LIGANDS AND COMPOSITIONS

This application is a Divisional Application of Ser. No. 09/399,252 filed Sep. 20, 1999.

FIELD OF THE INVENTION

This invention relates to a process for the preparation of linear aldehydes by hydroformylation of $C_2$ to $C_{20}$ monoethylenically unsaturated organic compounds in the presence of a Group VIII transition metal and selected multidentate phosphite ligands. The invention also relates to the selected multidentate phosphite ligands themselves, as well as hyroformylation catalysts made therefrom.

BACKGROUND OF THE INVENTION

Phosphorus-based ligands are ubiquitous in catalysis and are used for a number of commercially important chemical transformations. Phosphorus-based ligands commonly used in catalysis include phosphines and phosphites. These ligands include monophosphine and monophosphite ligands, which are compounds that contain a single phosphorus atom that serves as a donor to a transition metal, and bisphosphine, bisphosphite, and bis(phosphorus) ligands, which contain two phosphorus donor atoms and normally form cyclic chelate structures with transition metals.

An industrially important catalytic reaction using phosphorus-based ligands is olefin hydroformylation. Phosphite ligands are particularly good ligands for these reactions. For example, U.S. Pat. No. 5,235,113 describes a hydroformylation process in which an organic bidentate ligand containing two phosphorus atoms linked with an organic dihydroxyl bridging group is used in a homogeneous hydroformylation catalyst system also comprising rhodium. This patent describes a process for preparing aldehydes by hydroformylation of ethylenically unsaturated organic compounds, for example 1-octene or dimerized butadiene, using the above catalyst system. The use of phosphite ligands with rhodium has been disclosed in the hydroformylation of functionalized ethylenically unsaturated compounds. See for example Cuny et al., *J. Am. Chem. Soc.*, 1993, 115, 2066; U.S. Pat. Nos. 4,769,498, 4,668,651, 4,885,401, 5,113,022, 5,059,710, 5,235,113, 5,264,616, and 4,885,401; and published international applications WO9303839, and WO9518089.

Hydroformylation processes involving organic bidentate ligands containing an aromatic dihydroxyl bridging group and terminal aryl groups bearing heteroatom substituents are described in German Patent Application DE 19717359 A1.

Hydroformylation processes involving organic bidentate ligands containing two trivalent phosphorus atoms, in which the two phosphorous atoms are linked with a 2,2'-dihydroxyl-1,1'-binaphthalene bridging group, are described in U.S. Pat. No. 5,874,641 and the prior art referenced therein. U.S. Pat. No. 5,874,641 describes ligands containing substituents such as esters or ketones on the 3,3'-positions of the 2,2'-dihydroxyl-1,1'-binaphthalene bridging group. Such ligands provide reasonably good selectivity in the hydroformylation of internal olefins to terminal aldehydes.

Although some of these prior art systems involve commercially viable catalysts, there remains a need for even more effective catalyts to achieve even greater commercial potential. An object of this invention is to provide such improved catalysts for hydroformylation.

SUMMARY OF THE INVENTION

In one aspect, the present invention is a process for converting a $C_2$ to $C_{20}$ acyclic monoethylenically unsaturated compound to its corresponding terminal aldehyde, comprising reacting the compound with CO and $H_2$ in the presence of a Group VIII transition metal and at least one multidentate phosphite ligand of the following formulae I, II or III:

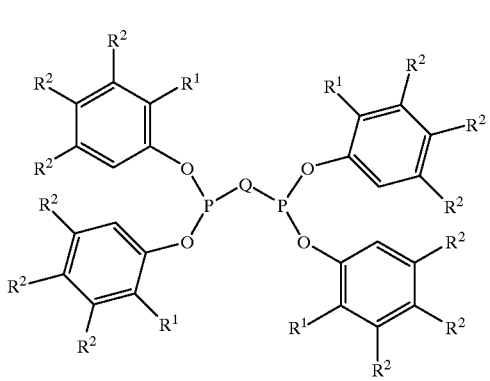

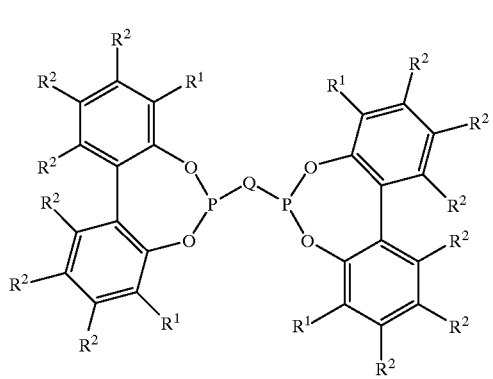

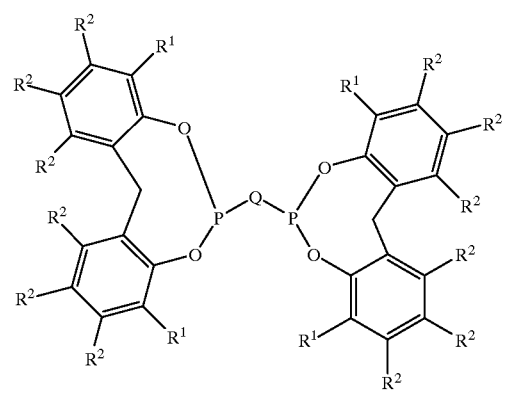

wherein:
each $R^1$ independently is $C_1$ to $C_{12}$ alkyl, $C_6$ to $C_{20}$ aryl, F, Cl, —$CO_2R^4$, —$OR^4$, or —$R^3Z$, provided that at least one $R^1$ is —$R^3Z$;
each $R^2$ independently is H, F, Cl, $C_1$ to $C_{12}$ alkyl, $C_6$ to $C_{20}$ aryl, —$OR^4$, —$CO_2R^4$, —$C(O)R^4$, —CHO, —CN, or —$CF_3$;
each $R^3$ independently is $C_1$ to $C_{10}$ alkylene;
each $R^4$ independently is $C_1$ to $C_{12}$ alkyl or $C_6$ to $C_{20}$ aryl;
each Z is —$CO_2R^4$, —CHO, —$C(O)R^4$, —$C(O)SR^4$, —$SR^4$, —$C(O)NR^5R^6$, —$OC(O)R^4$, —$OC(O)OR^4$, —N=CR⁵R⁶, —C(R⁵)=NR⁶, —C(R⁵)=N—O—R⁶, —P(O) (OR⁴) (OR⁴), —S(O)₂R⁴, —S(O)R⁴, —C(O) OC(O)R⁴, —NR⁴CO₂R⁴, —NR⁴C(O)NR⁵R⁶, or —CN;

each R⁴ independently is $C_1$ to $C_{12}$ alkyl or $C_6$ to $C_{20}$ aryl;
each R⁵ independently is H, $C_1$ to $C_{12}$ alkyl, or $C_6$ to $C_{20}$ aryl;
each R⁶ independently is H, $C_1$ to $C_{12}$ alkyl, or $C_6$ to $C_{20}$ aryl;
Q is a divalent bridging group of the formula:

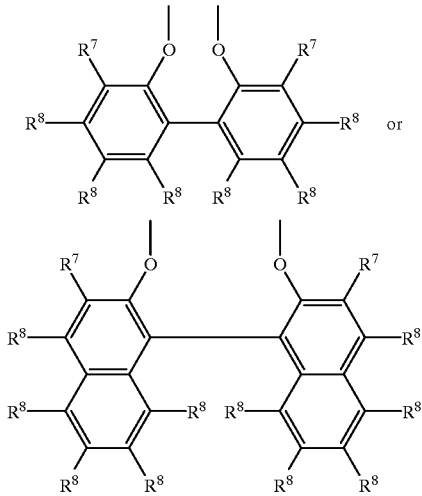

wherein:
each R⁷ independently is H, F, Cl, $C_1$ to $C_{12}$ alkyl, $C_6$ to $C_{20}$ aryl, —OR⁴, —CO₂R⁴, —C(O)R⁴, —C(R⁵)=N—O—R⁶, —CHO, —CN, —CF₃, —C(R⁵)=NR⁶, —NR⁵R⁶ or —R³Z; and
each R⁸ is H, F, Cl, $C_1$ to $C_{12}$ alkyl, $C_6$ to $C_{20}$ aryl, —OR⁴, —CO₂R⁴, —C(O)R⁴, —CN, or —CF₃.

The term "aryl" is meant to denote an organic radical which is derived from an aromatic hydrocarbon by removal of one atom. Suitable aryl radicals are, for example, phenyl, benzyl, naphthyl, binaphthyl, and anthracenyl. The terms "alkyl" and "alkylene" are meant to denote both straight and branched groups.

In another aspect, this invention provides for the above multidentate phosphite ligands and catalyst compositions made therefrom.

Any of the above ligands optionally may be attached to a soluble or insoluble inert support. An example of an insoluble inert support is Merrifield's resin (a functionalized polystyrene resin commercially available from Aldrich Chemical Company).

DETAILED DESCRIPTION OF THE INVENTION

This invention provides a process for the preparation of terminal aldehydes with high catalyst performance (selectivity and/or activity). The advantages of the present process are particularly pronounced when the reactant is an internally monoethylenically unsaturated compound. Preparing terminal aldehydes starting from internally monoethylenically unsaturated compounds using previously known hydroformylation processes generally results in moderate selectivity to terminal aldehydes, some hydrogenation of the double bond and/or lower catalytic activity. An additional advantage of the process according to the present invention is that the linearity [terminal aldehydes/(terminal+branched aldehydes)] is high, facilitating the isolation of the desired terminal aldehyde from a mixture of terminal and branched aldehydes.

The catalyst compositions useful in the processes of the invention comprise selected multidentate phosphite ligands and a Group VIII transition metal, which is provided in the form of a chemical compound.

The multidentate phosphite ligand is of the formulae I, II or III:

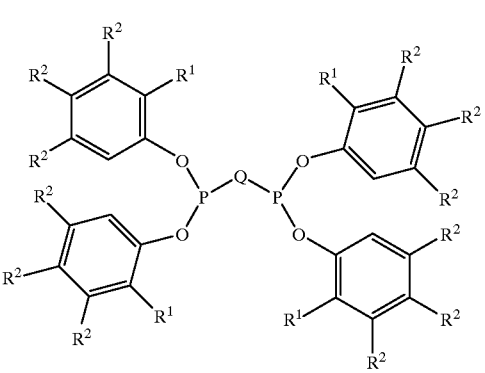

I

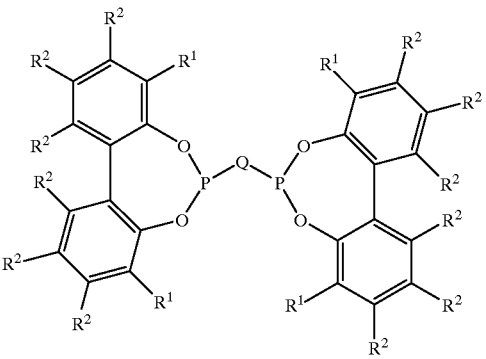

II

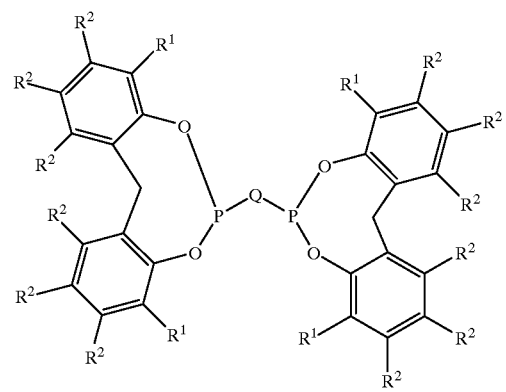

III wherein:
each R¹ independently is $C_1$ to $C_{12}$ alkyl, $C_6$ to $C_{20}$ aryl, F, Cl, —CO₂R⁴, —OR⁴, or —OR³Z, provided that at least one R¹ is —R³Z;

each $R^2$ independently is H, F, Cl, $C_1$ to $C_{12}$ alkyl, $C_6$ to $C_{20}$ aryl, $-OR^4$, $-CO_2R^4$, $-C(O)R^4$, $-CHO$, $-CN$, or $-CF_3$;

each $R^3$ independently is $C_1$ to $C_{10}$ alkylene;

each $R^4$ independently is $C_1$ to $C_{12}$ alkyl or $C_6$ to $C_{20}$ aryl;

each Z is $-CO_2R^4$, $-CHO$, $-C(O)R^4$, $-C(O)SR^4$, $-SR^4$, $-C(O)NR^5R^6$, $-OC(O)R^4$, $-OC(O)OR^4$, $-N=CR^5R^6$, $-C(R^5)=NR^6$, $-C(R^5)=N-O-R^6$, $-P(O)(OR^4)(OR^4)$ $-S(O)_2R^4$, $-S(O)R^4$, $-C(O)OC(O)R^4$, $-NR^4CO_2R^4$, $-NR^4C(O)NR^5R^6$, or or $-CN$;

each $R^4$ independently is $C_1$ to $C_{12}$ alkyl or $C_6$ to $C_{20}$ aryl;

each $R^5$ independently is H, $C_1$ to $C_{12}$ alkyl, or $C_6$ to $C_{20}$ aryl;

each $R^6$ independently is H, $C_1$ to $C_{12}$ alkyl, or $C_6$ to $C_{20}$ aryl;

Q is a divalent bridging group of the formula:

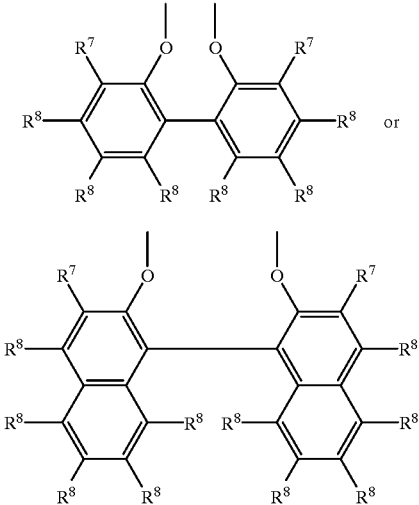

wherein:
each $R^7$ independently is H, F, Cl, $C_1$ to $C_{12}$ alkyl, $C_6$ to $C_{20}$ aryl, $-OR^4$, $-CO_2R^4$, $-C(O)R^4$, $-(R^5)=N-O-R^6$, $-CHO$, $-CN$, $-CF_3$, $-C(R^5)=NR^6$, $-NR^5R^6$ or $-R^3Z$; and each $R^8$ is H, F, Cl, $C_1$ to $C_{12}$ alkyl, $C_6$ to $C_{20}$ aryl, $OR^4$, $-CO_2R^4$, $-C(O)R^4$, $-CN$, or $-CF_3$.

Preferred multidentate phosphite ligands are of the following formula I:

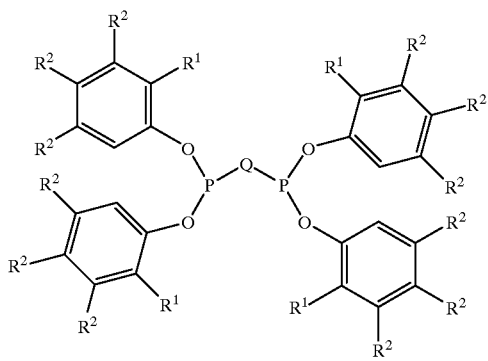

wherein:
each $R^1$ independently is $-R^3Z$;
each $R^2$ independently is H, F, Cl, $C_1$ to $C_{12}$ alkyl, $C_6$ to $C_{20}$ aryl, $-OR^4$, $-CO_2R^4$, $-C(O)R^4$, $-CHO$, $-CN$, or $-CF_3$;
each $R^3$ independently is $C_1$ to $C_4$ alkylene;
each Z independently is $-CO_2R^4$, $-CHO$, $-C(O)R^4$, $-C(O)NR^5R^6$, $-OC(O)R^4$, $-OC(O)OR^4$, $-N=CR^5R^6$, or $-C(R^5)=NR^6$;
Q is a divalent bridging group of the formula:

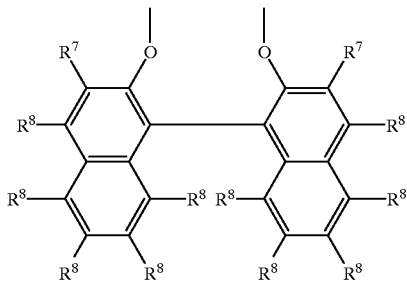

wherein:
each $R^7$ independently is $-CO_2R^4$, $-C(O)R^4$, $-C(R^5)=N-O-R^6$, $-CHO$, $-CN$, or $-C(R^5)=N(R^6)$; and each $R^8$ independently is H, F, Cl, $C_1$ to $C_{12}$ alkyl, $C_6$ to $C_{20}$ aryl, $-OR^4$, $-CO_2R^4$, $-C(O)R^4$, $-CN$, or $-CF_3$.

The multidentate phosphite ligands of the present invention can be prepared by using a process in which a phosphorochloridite is reacted with a divalent bridging group. The phosphorochloridite can be prepared by treating at a temperature between about −40° C. and 10° C. one molar equivalent of $PCl_3$ with about two molar equivalents of substituted phenol in the absence of an organic base. The resulting solution is then treated with at least two equivalents of an organic base to produce a phosphorochloridite. When the substituted phenols are replaced with substituted biphenol or substituted alkylidenebisphenol, the phosphorochloridite is similarly prepared from initially mixing one molar equivalent of $PCl_3$ with about one molar equivalent of substituted biphenol or substituted alkylidenebisphenol between about −40° C. and 10° C. in the absence of an organic base. The resulting solution is then treated with at least two equivalents of an organic base to produce a phosphorochloridite.

When preparing the phosphorochloridite in the above manner, it is important to maintain temperature in the −40° C. and 10° C. range during the base addition. The addition of base results in the formation of an insoluble salt formed by neutralizing HCl, and the reaction mixture can become a thick slurry. Such a slurry can create problems in achieving good mixing of base which is important in avoiding temperature gradients in the reaction mixture which can decrease yield of the desired product. It is important, therefore, that the reaction be conducted with vigorous stirring or other agitation to allow effective removal of heat from the reaction mixture. Cooling to the required temperature range can be accomplished by well-known techniques in the art.

At a temperature range between −40° C. and 70° C., the phosphorochloridite is reacted with about a half molar equivalent of the divalent bridging group. If less than three equivalents of the organic base were utilized in preparing the phosphorochloridite, additional organic base is added to bring the total equivalents of organic base utilized in the process to at least three.

The base used in preparing the multidentate phosphite ligands should be anhydrous and soluble in the reaction medium. Suitable bases are organic amines. Especially preferred are trialkylamines. The most preferred bases are selected from the group consisting of tributylamine, benzyldimethylamine, triethylamine, and diisopropylmethylamine.

The phosphorochloridites can be prepared by a variety of other methods known in the art. One method involves treating phenols with $PCl_3$, such as described in, Polymer 1992, 33, 161; *Inorganic Syntheses,* 1966, 8, 68; U.S. Pat. No. 5,210,260; and *Z. Anorg. Allg. Chem.,* 1986, 535, 221.

When the phosphorochloridite cannot be prepared in good yield from $PCl_3$, the preferred method involves the treatment of N,N-dialkyl diarylphosphoramidite derivatives with HCl. The N,N-dialkyl diarylphosphoramidite is of the form $(R^9)_2NP(aryloxy)_2$ where $R^9$ is a $C_1$ to $C_4$ alkyl group, and can be obtained by reacting phenol or substituted phenol with $(R^9)_2NPCl_2$ by methods known in the art, such as described in WO9622968, U.S. Pat. Nos. 5,710,306, and 5,821,378. The N,N-dialkyl diarylphosphoramidites may be prepared, for example, as described in *Tet. Lett.,* 1993, 34,6451; Synthesis, 1988, 2, 142–144, and *Aust. J. Chem.,* 1991, 44, 233.

The multidentate phosphite ligand does not have to be pure to be used in the process of the present invention; it can contain some monodentate phosphites as impurities.

Multidentate phosphite ligands may be supported on soluble or insoluble inert supports. Polymer-supported multidentate phosphorus ligands may be prepared by a variety of methods known in the art. See WO9303839, U.S. Pat. Nos. 4,769,498 and 4,668,651, and WO9906146. In general, the preparation involves the reaction of a phosphorus halide, typically but not limited to, chloride, with a diol to form P—O bonds. A representative example is shown below.

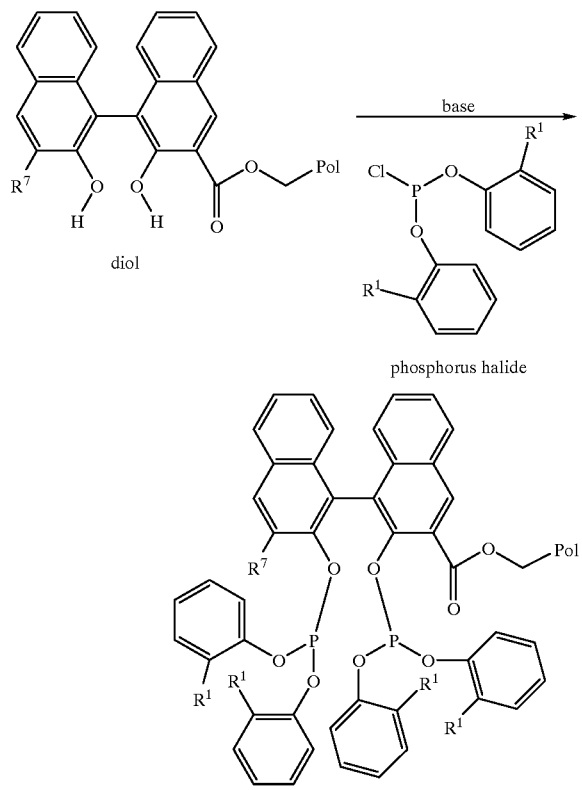

"Pol" denotes the soluble or insoluble inert support. $R^1$ and $R^7$ are as defined above.

A specific example of an insoluble inert support is Merrifield's resin (a functionalized polystyrene resin available from Aldrich Chemical Company). The above diol may be prepared by first partial esterification of 2,2'-dihydroxyl-1, 1'-binaphthalene-3,3'-dicarboxylic acid with Merrifield's resin, followed by esterification of the resulting ester/acid diol intermediate. The esterification conditions are well known to those skilled in the art of organic synthesis.

The invention also provides for certain multidentate phosphite ligands and catalyst compositions made therefrom. In particular, these include the ligands of Formula I, II or III and the combination of a ligand of Formula I, II or III with a Group VIII transition metal compound. Preferred Group VIII transition metals are rhodium, cobalt, iridium, palladium and platinum, the most preferred being rhodium. The Group VIII metal is provided in the form of a compound, such as a hydride, halide, organic acid salt, ketonate, inorganic acid salt, oxide, carbonyl compound or amine compound. Preferred Group VIII metal compounds are $Ir_4(CO)_{12}$, $IrSO_4$, $RhCl_3$, $Rh(NO_3)_3$, $Rh(OAc)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, and $[RhCl(COD)]_2$ (wherein "acac" is an acetylacetonate group; "OAc" is an acetyl group; "COD" is 1,5-cyclooctadiene; and "Ph" is a phenyl group). However, it should be noted that the Group VIII metal compounds are not necessarily limited to the above listed compounds. The rhodium compounds, suitable for hydroformylation, can be prepared or generated according to techniques well known in the art, as described, for example, in WO 95 30680, U.S. Pat. No. 3,907,847, and *J. Amer. Chem. Soc.,* 115, 2066, 1993. Rhodium compounds that contain ligands which can be displaced by the present multidentate phosphite ligands are a preferred source of rhodium. Examples of such preferred rhodium compounds are $Rh(CO)_2$ (acac), $Rh(CO)_2(C_4H_9COCHCO-t-C_4H_9)$, $Rh_2O_3$, $Rh_4(CO)_{12}$, $Rh_6(CO)_{16}$, $Rh(O_2CCH_3)_2$, and Rh(2-ethylhexanoate).

The reactant of the present process is a monoethylenically unsaturated organic compound having at least one "C=C" bond in the molecule and preferably 2 to 20 carbon atoms. Examples of suitable ethylenically unsaturated organic compounds are linear terminal olefinic hydrocarbons, for example, ethylene, propylene, 1-butene, 1-pentene, 1-hexene, 1-octene, 1-nonene, 1-decene, 1-tetradecene, 1-hexadecene, 1-octadecene, 1-eicosene and 1-dodecene; branched terminal olefinic hydrocarbons, for example, isobutene and 2-methyl-1-butene; linear internal olefinic hydrocarbons, for example, cis- and trans-2-butene, cis- and trans-2-hexene, cis- and trans-2-octene, cis- and trans-3-octene; branched internal olefinic hydrocarbons, for example, 2,3-dimethyl-2-butene, 2-methyl-2-butene and 2-methyl-2-pentene; terminal olefinic hydrocarbons; internal olefinic hydrocarbon mixtures; for example, octenes, prepared by dimerization of butenes.

Examples of suitable olefinic compounds include those substituted with an unsaturated hydrocarbon group, including olefinic compounds containing an aromatic substituent such as styrene, alpha-methylstyrene and allylbenzene.

The ethylenically unsaturated organic compound can be substituted with one or more functional groups containing a heteroatom, such as oxygen, sulfur, nitrogen or phosphorus. Examples of these heteroatom-substituted ethylenically unsaturated organic compounds include vinyl methyl ether, methyl oleate, oleyl alcohol, 3-pentenenitrile, 4-pentenenitrile, 3-pentenoic acid, 4-pentenoic acid, methyl 3-pentenoate, 3-pentenal, allyl alcohol, 7-octen-1-al, acrylonitrile, acrylic acid esters, methyl acrylate, methacrylic acid esters, methyl methacrylate, and acrolein.

The invention is especially directed to hydroformylation processes in which a linear aldehyde compound is prepared starting from internal monoethylenically unsaturated organic compounds with 2 to 20 carbon atoms.

Preferred monoethylenically unsaturated compounds that are useful in the process of this invention are shown in Formulas IV and VI, and the corresponding terminal aldehyde compounds produced are illustrated by Formulas V and VII, respectively.

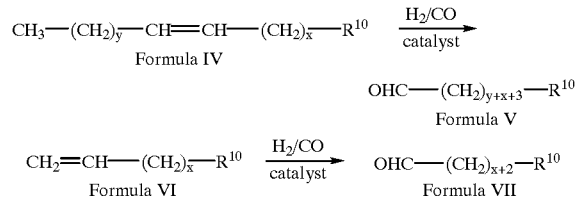

wherein $R^{10}$ is H, —CN, —$CO_2R^5$, —C(O)$NR^5R^6$, —CHO, —$OR^4$, or OH;

y is an integer from 0 to 12;

x is an integer from 0 to 12;

$R^4$, $R_5$ and $R^6$ are as defined above.

Particularly preferred internal monoethylenically unsaturated organic compounds are 3-pentenenitrile, 3-pentenoic acid, and alkyl 3-pentenoate, such as methyl 3-pentenoate. The linear aldehyde compound prepared by the present process starting with one of these compounds can be used advantageously in the preparation of ε-caprolactam, hexamethylenediamine, 6-aminocaproic acid, 6-aminocapronitrile or adipic acid, which are precursors for Nylon-6 and/or Nylon-6,6.

The 3-pentenenitrile may be present in mixtures containing 4-pentenenitrile. Similarly, when alkyl 3-pentenoate or 3-pentenoic acid is the reactant used in the present process, mixtures containing alkyl 4-pentenoate or 4-pentenoic acid, respectively, may be present. Because the 4-isomers of these compounds react in a similar fashion as their corresponding 3-isomers to the desired linear aldehyde, a mixture of isomers can be used directly in the present process. Hydroformylation of these 3- and 4-isomer can be carried out in the presence of 2-isomers. Impurities can be present as long as they do not interfere with the reaction.

The hydroformylation process according to the invention can be performed as described below.

The reaction conditions of the hydroformylation process are, in general, the same as those used in a conventional process, described for example in U.S. Pat. No. 4,769,498, and will be dependent on the particular starting monoethylenically unsaturated organic compound. For example, the temperature can be from ambient temperature to 200° C., preferably from about 50 to 150° C., and more preferably from 85° to 110° C. The pressure may vary from normal pressure to 5 MPa, preferably from 0.1 to 2 MPa. The pressure is, as a rule, equal to the combined hydrogen and carbon monoxide partial pressures. However, extra inert gases may also be present; the pressure may vary from normal pressure to 15 MPa when inert gases are present. The molar ratio of hydrogen to carbon monoxide is generally between 10:1 and 1:10, and preferably between 6:1 and 1:2.

The amount of transition metal compound is selected so that favorable results can be obtained with respect to catalyst activity and process economy. In general, the concentration of transition metal in the reaction medium is between 10 and 10,000 ppm and more preferably between 50 and 1000 ppm, calculated as free metal.

The molar ratio of phosphorus ligand to transition metal is selected so that favorable results can be obtained with respect to catalyst activity and desired aldehdye selectivity. This ratio generally is from about 0.5 to 100 and preferably from 1 to 20 (moles phosphorus per mole metal).

The solvent may be the mixture of reactants of the hydroformylation reaction itself, such as the starting unsaturated compound, the aldehyde product and/or by-products. Other suitable solvents include saturated hydrocarbons (for example, kerosene, mineral oil, or cyclohexane), ethers (for example, diphenyl ether or tetrahydrofuran), ketones (for example, acetone, cyclohexanone), nitrites (for example, acetonitrile, adiponitrile or benzonitrile), aromatics (for example, toluene, benzene, or xylene), esters (for example, methyl valerate, caprolactone), Texanol® (Union Carbide), or dimethylformamide.

EXAMPLES

The following non-limiting examples further illustrate the invention. All percentages are on a mole basis, unless otherwise noted.

Example 1

Synthesis of Ligand 1

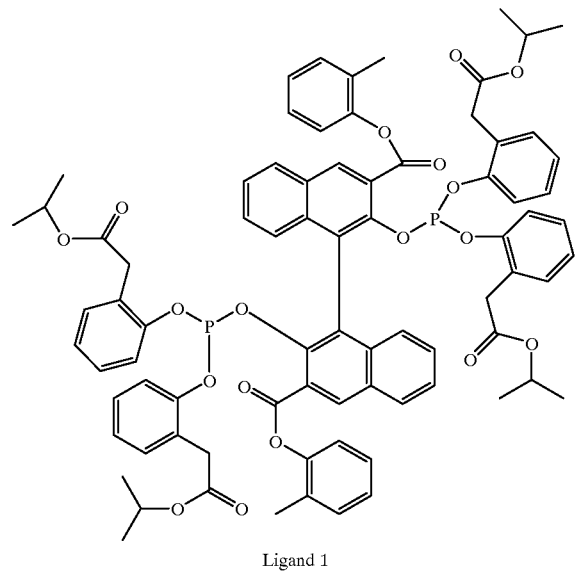

Ligand 1

Isopropyl 2-hydroxyphenyl acetate was prepared using the procedure described in J. Amer. Chem. Soc., 70, 1948, 1930. To a flask were added 10 g of 2-hydroxy phenylacetic acid, 99 mL of isopropanol and 9.9 mL of concentrated sulfuric acid. The mixture was refluxed for 5.5 hrs, poured into 400 mL of ice and extracted with 3×100 mL of ether. The organic layer was washed with 100 mL of aqueous solution of sodium bicarbonate (saturated). The organic fraction was dried over sodium sulfate and the solvent removed by rotary evaporation. The residue was flash chromatographed on silica gel eluted with 10% ethyl acetate/hexane to give 9.227 g of the desired product as a white solid. $^1$H NMR (300 Mhz, δ, $CDCl_3$): 7.16 (m, 1H), 7.08 (dd, 1H), 6.92 (dd, 1H), 6.80 (m, 1H), 5.04 (septet, J=6.2 Hz, 1H), 3.60 (s, 2H), 1.25 (d, 6.2 Hz, 6H).

The above phenol (4.8 g) was dissolved in 100 mL diethyl ether, and cooled to −40° C. in a nitrogen purged glove box. Triethylamine (3.0 g) was added, followed by the addition of 2.1 g of diethyl phosphoramidous dichloride. Upon addition of diethyl phosphoramidous dichloride, a white precipitate formed. The reaction mixture was stirred at room temperature for one hour, then filtered over a pad of Celite® (filter aid manufactured by Johns Manville Corp.). The filtrate was concentrated in vacuo to yield 5.8 g (96%) of the corresponding phosphorous amidite. $^{31}$P NMR (toluene) 141.7 ppm.

The above phosphorous amidite (5.8 g) was dissolved in 100 mL anhydrous ether and cooled to −40° C. To the stirring amidite solution was added 23 mL of pre-cooled 1M HCl solution in ether via an addition funnel. Upon addition, white precipitate formed. The mixture was stirred for 10 minutes, and cooled back to −40° C. for 2 hours. The resulting slurry was filtered over a pad of Celite®, and concentrated in vacuo to yield 5.1 g of the corresponding phosphorochloridite. $^{31}$P NMR (toluene): 162.1 ppm.

The above phosphorochloridite (5.12 g, 11 mmol) was dissolved in cold ether (30 mL) and cooled to −30° C. To this was added di-o-tolyl 2,2'-dihydroxyl-1,1'-binaphthalene-3,3'-dicarboxylate (2 g, 3.61 mmol) while stirring, followed by dropwise addition of triethylamine solution (1.1 g in 5 mL ether). After the addition, the mixture was stirred at room temperature for 15 minutes, then left standing at −30° C. overnight to yield a white slurry. The product was filtered through a pad of neutral alumina, and the filtrate was concentrated in vacuo to give a waxy white solid. This solid was washed with hexanes to yield 2.0 g of white powder. $^{31}$P NMR (toluene): major resonance at 129.4 ppm, along with minor peaks at 127.1, 131.3 ppm.

Example 1A

Hydroformylation of 3-Pentenenitrile with Ligand 1/Rhodium bis(carbonyl)acetylacetonate A solution containing 1.09 g of Ligand 1, 0.040 g of rhodium bis(carbonyl) acetylacetonate, 2 g of ortho-dichlorobenzene (GC internal standard) and 70 g of 3-pentenenitrile was mixed and stirred with 3 g of Amberlyst® A-21 ion-exchange resin (weakly basic, macroreticular resin available manufactured by Rohm and Haas) for 15 minutes. The resin was removed by filtration and the solution loaded into a 100 mL autoclave and heated with vigorous stirring under 0.45 MPa with a 1:1 mixture of CO and $H_2$ under flowing CO/$H_2$ at a rate of 20 mL/min at 95° C. for 6 hours. A sample was removed from the reactor after 6 hours and analyzed by gas chromatography using an HP 5890A Chromatograph with a Quadrex 23 fused silica capillary column (30 meters, 0.32 mm I.D., 0.25 um film thickness) purchased from the Quadrex Corporation. GC analysis: (mole %): 2-pentenenitrile 2.13%, valeronitrile 8.1%, 3-pentenenitrile 8%, 5-formylvaleronitrile 70.2%. "Conversion" is the percentage of 3- and 4-pentenenitrile which is converted to products. "Selectivity" is the percentage of the product mixture that is comprised of 5-formylvaleronitrile, and "linearity" is the percentage the aldehyde products that is comprised of 5-formylvaleronitrile. Conversion of pentenenitriles: 92%; selectivity to 5-formylvaleronitrile: 78% on a mole basis; linearity of aldehydes produced: 87%.

Example 1B

Hydroformylation of Methyl 3-Pentenoate with Ligand 1/Rhodium bis(carbonyl)acetylacetonate In a drybox was prepared a solution containing methyl 3-pentenoate (0.5 M), rhodium bis(carbonyl)acetylacetonate (1.0 mM), and 1,2-dichlorobenzene (internal standard, 0.14 M) in toluene. A portion of this solution was added to a glass-lined pressure vessel and enough of a solution of the ligand (0.05 M) in toluene was added to give 4.6 equivalents of Ligand 1 to Rh. The reactor was sealed, pressurized to 0.45 MPa with a 1:1 mixture of CO and $H_2$ and heated to 95° C. for 3 hours. The reactor was cooled and depressurized, and a sample of the reaction mixture was analyzed by gas chromatography on an HP 5890A Chromatograph with a DB-FFAP fused silica capillary column (30 meters, 0.32 mm I.D., 0.25 um film thickness) purchased from JW Scientific. GC analysis: (mole %) methyl-2-pentenoate 5.6%, methyl valerate 1.7%, methyl-3-pentenoate 28.3%, methyl-5-formylvalerate 62.2%. Conversion of methyl pentenoates: 71%; selectivity to methyl-5-formylvalerate: 88% on a mole basis; linearity of aldehydes produced: 98%.

Example 2

Synthesis of Ligand 2

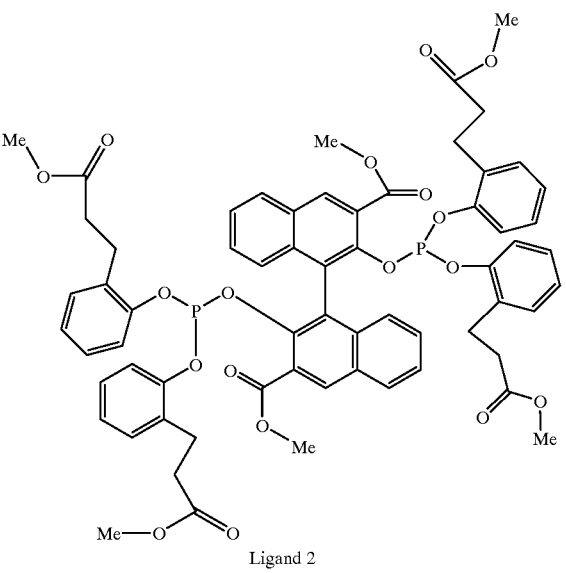

Ligand 2

The phosphorochloridite of methyl 3-(2-hydroxyphenyl) proprionate was prepared from $PCl_3$ in toluene with triethylamine as base at −30° C. $^{31}$P NMR of the reaction mixture: 162.8 ppm. To this mixture was added dimethyl 2,2'-dihydroxyl-1,1'-binaphthalene-3,3'-dicarboxylate and more triethylamine. The mixture was filtered through Celite® and the solvent removed by rotary evaporation. The residue was dissolved in toluene and passed through basic alumina with toluene. The solvent was removed and the residue passed through silica gel with toluene and then tetrahydrofuran. Solvent was removed from the tetrahydrofuran fraction and the residue vacuum dried. $^{31}$P {H} NMR (202.4 MHz, $CDCl_3$): major resonance at 131.0 ppm with minor other resonances at 147.0 and 131.4 ppm.

Example 2A

Hydroformylation of 3-Pentenenitrile with Ligand 2/Rhodium bis(carbonyl)acetylacetonate A solution containing 0.018 g of rhodium bis(carbonyl) acetylacetonate, 3.7 equivalents of Ligand 2 to Rh, 1 g of ortho-dichlorobenzene and 30 g of 3-pentenenitrile was loaded into a 100 mL autoclave and heated with vigorous stirring under 0.45 MPa with a 1:1 mixture of CO and $H_2$ while flowing $CO/H_2$ at a rate of approximately 30 mL/min at 95° C. for 5 hours. The reactor was cooled and depressurized, and a sample of the reaction mixture was analyzed by gas chromatography on an HP 5890A Chromatograph with a Quadrex 23 fused silica capillary column (30 meters, 0.32 mm I.D., 0.25 um film thickness) purchased from the Quadrex Corporation. GC analysis: (mole %) 2-pentenenitrile 3.6%, valeronitrilel 5.4 %, 3-pentenenitrile 7.5%, 5-formylvaleronitrile 53.5%. Conversion of pentenenitriles: 92%; selectivity to 5-formylvaleronitrile: 58% on a mole basis; linearity of aldehydes produced: 73%.

Example 2B

Hydroformylation of Methyl 3-Pentenoate with Ligand 2/Rhodium bis(carbonyl)acetylacetonate Reaction was run as in example 1B, but with 4.6 equivalents of Ligand 2 to Rh. GC analysis: (mole %) methyl-2-pentenoate 6.4%, methyl valerate 3.2%, methyl-3-pentenoate 21.2%, methyl 5-formylvalerate 66.4%. Conversion of methyl pentenoates: 79%; selectivity to methyl 5-formylvalerate: 84% on a mole basis; linearity of aldehydes produced: 96%.

Example 3

Synthesis of Ligand 3

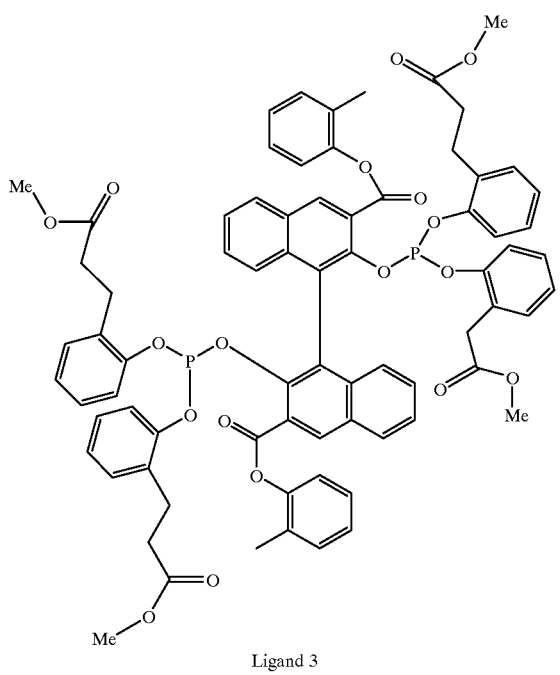

Ligand 3

The same procedure as example 2 was followed, but with di-o-tolyl 2,2'-dihydroxyl-1,1'-binaphthalene-3,3'-dicarboxylate instead of dimethyl 2,2'-dihydroxyl-1,1'-binaphthalene-3,3'-dicarboxylate. $^{31}P$ {H} nmr (202.4 MHz, $CDCl_3$): major resonance at 129.4 ppm with minor resonances at 148.3 and 131.4 ppm

Example 3A

Hydroformylation of 3-Pentenenitrile with Ligand 3/Rhodium bis(carbonyl)acetylacetonate Reaction was run as in example 2A, but with 3.7 equivalents of Ligand 3 to Rh for 5 hours. GC analysis: (mole %) 2-pentenenitrile 1.8%, valeronitrile 19.0%, 3-pentenenitrile 4.0%, 5-formylvaleronitrile 60.5%. Conversion of pentenenitriles: 96%; selectivity to 5-formylvaleronitrile: 63% on a mole basis; linearity of aldehydes produced: 81%.

Example 3B

Hydroformylation of Methyl-3-Pentenoate with Ligand 3/Rhodium bis(carbonyl)acetylacetonate Reaction was run as in example 1B, but with 4.6 equivalents of Ligand 3 to Rh. GC analysis: (mole %) methyl 2-pentenoate 4.3%, methyl valerate 1.5%, methyl 3-pentenoate 36.9%, methyl 5-formylvalerate 54.5%. Conversion of methyl pentenoates: 62%; selectivity to methyl 5-formylvalerate: 88% on a mole basis; linearity of aldehydes produced: 96%.

Example 4

Synthesis of Ligand 4

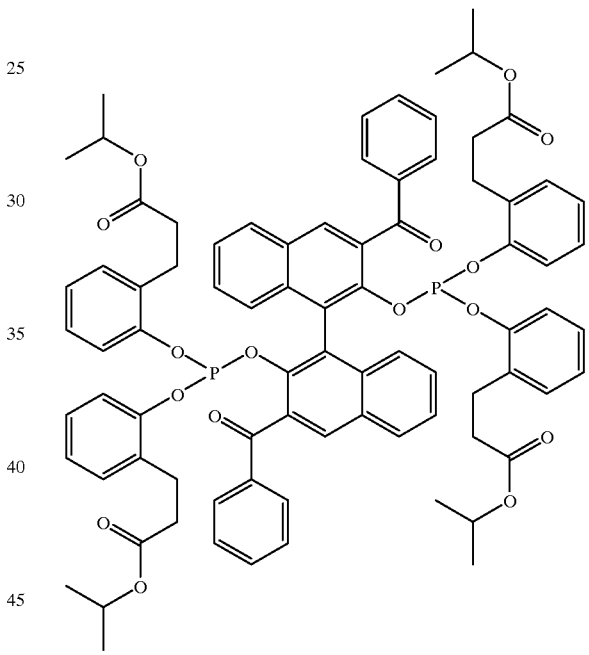

Ligand 4

With stirring under dry nitrogen, 2,2'-dihydroxy-1,1'-binaphthalene-3,3'-dicarboxylic acid (8.42 g, 22.5 mmol) was dissolved in dry tetrahydrofuran (500 mL) then cooled to −78° C. with a dry ice/acetone bath. Phenyllithium (100 mL of 1.8 M in 70/30 cyclohexane/ether, 0.18 mol) was added dropwise, then the solution was allowed to warm to ambient temperature. After stirring overnight, deionized water (50 mL) was slowly added to the reaction solution at 0° C. With vigorous stirring, 1 M hydrochloric acid was added dropwise until the water phase became strongly acidic (pH=2). The organic phase was washed with water in a separatory funnel, then dried over magnesium sulfate and evaporated. The orange residue was redissolved in dichloromethane and eluted through a silica gel plug. The orange filtrate was evaporated to yield 2,2'-dihydroxy-1,1'-binaphthalene-3,3'-bis(phenylketone) as a yellow solid (10.5 gm).

The phosphorochloridite of isopropyl 3-(2-hydroxyphenyl)prioprionate was prepared as described in example 1. $^{31}$P NMR (toluene):δ163. 2,2'-Dihydroxy-1,1'-binaphthalene-3,3'-bis(phenylketone) was added to the phosphorochloridite of isopropyl 3-(2-hydroxyphenyl) prioprionate in the presence of triethylamine, following the procedure outlined in example 1 to yield Ligand 4. $^{31}$P NMR (toluene):δ127 (major), 123 (minor).

Example 4A

Hydroformylation of 3-Pentenenitrile with Ligand 4/Rhodium bis(carbonyl)acetylacetonate In a drybox was prepared a solution containing 3-pentenenitrile (0.5 M), rhodium bis(carbonyl) acetylacetonate (0.85 mM), and 1,2-dichlorobenzene (internal standard, 0.14 M) in toluene. A portion of this solution was added to a glass-lined pressure vessel and enough of a solution of the ligand (0.05 M) in toluene was added to give 2.9 equivalents of Ligand 4 to Rh. The reactor was sealed, pressurized to 0.45 MPa with a 1:1 mixture of CO and H$_2$ and heated to 95° C. for 3 hours. The reactor was cooled and depressurized, and a sample of the reaction mixture was analyzed by gas chromatography on an HP 5890A Gas Chromatograph with a Quadrex 23 fused silica capillary column (30 meters, 0.32 mm I.D., 0.25 um film thickness) purchased from the Quadrex Corporation. GC analysis: (mole %) 2-pentenenitrile 7.2%, valeronitrile 9.9%, 3-pentenenitrile 24.7%, 5-formylvaleronitrile 53.6%. Conversion of pentenenitriles: 78%; selectivity to 5-formylvaleronitrile: 72% on a mole basis; linearity of aldehydes produced: 90%.

Example 5

Synthesis of Ligand 5

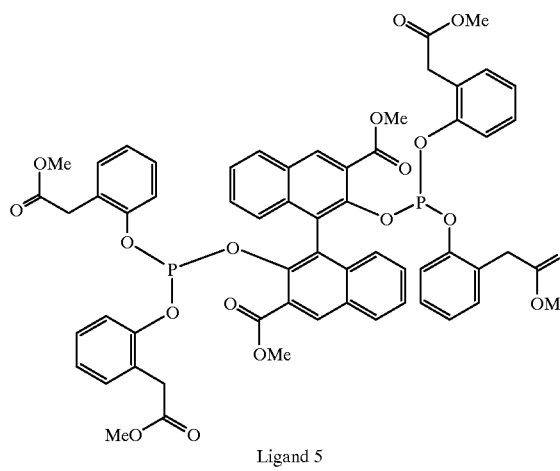

Ligand 5

The reaction was carried out in an inert atmosphere. In a 100 mL flask was added 0.206 g of phosphorus trichloride and 16 g of toluene. The mixture was cooled to −30° C. and 0.499 g of methyl 2-hydroxyphenyl acetate was added. To this cooled solution was added dropwise 0.400 g of triethylamine in 8 g of toluene which had been cooled to −30° C. After addition of the triethylamine, 0.605 g of dimethyl 2,2'-dihydroxyl-1,1'-binaphthalene-3,3'-dicarboxylate was added along with 0.300 g of triethylamine. The mixture was stirred overnight, filtered over Celite® (Johns Manville Corp.), and solvent removed by rotary evaporation. A thick yellow oil (1.274 g) was obtained. $^{31}$P {H} NMR (202.4 MHz, CDCl$_3$) indicated a mixture: 145.8, 130.9, 130.4, 129.4, 129.0 ppm. Matrix Assisted Laser Desorption Ionization Mass Spectroscopy (MALDI MS): found M$^+$+Na: 1144.5; calculated for C$_{60}$H$_{52}$O$_{18}$P$_2$+Na: 1145.2

Example 5A

Hydroformylation of 3-Pentenenitrile with Ligand 5/Rhodium bis(carbonyl)acetylacetonate Reaction was run as in example 4A, but with 5.4 equivalents of Ligand 5 to Rh. GC analysis: (mole %) 2-pentenenitrile 5.6%, valeronitrile 7.9%, 3-pentenenitrile 21.7%, 5-formylvaleronitrile 61.7%. Conversion of pentenenitriles: 86%; selectivity to 5-formylvaleronitrile: 79% on a mole basis; linearity of aldehydes produced: 95%.

Example 5B

Hydroformylation of Methyl-3-Pentenoate with Ligand 5/Rhodium bis(carbonyl)acetylacetonate Reaction was run as in example 1B, but with 4.6 equivalents of Ligand 5 to Rh. GC analysis: (mole %) methyl 2-pentenoate 6.8%, methyl valerate 3.4%, methyl 3-pentenoate 17.4%, methyl 5-formylvalerate 70.1%. Conversion of methyl pentenoates: 82%; selectivity to methyl 5-formylvalerate: 85% on a mole basis; linearity of aldehydes produced: 97%.

Example 6

Synthesis of Ligand 6

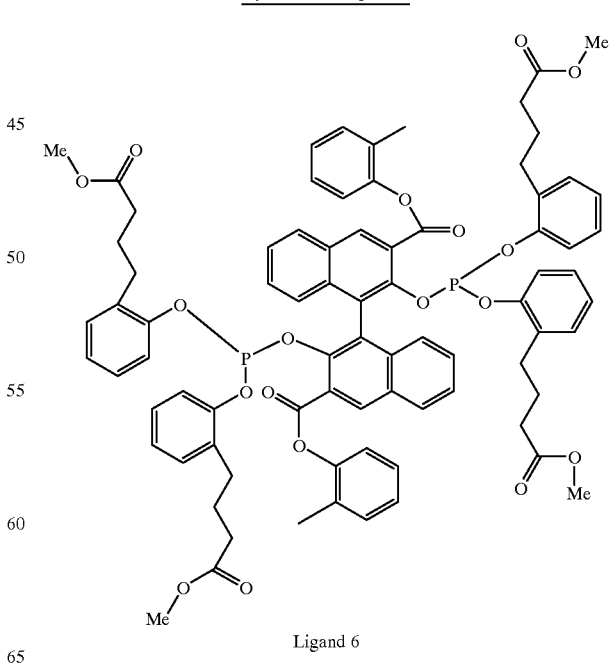

Ligand 6

4-(2-Hydroxyphenyl)butyric acid (1 g, 5.55 mmol) was dissolved in 20 mL anhydrous methanol, and 5 mL sulfuric acid. The mixture was heated to reflux for 6 hours. After aqueous workup, 1.14 g of methyl 4-(2-hydroxyphenyl) butyrate was obtained. $^1$H NMR (CDCl$_3$): 1.92 (q, 2H), 2.40 (t, 2H), 2.65 (t, 2H), 3.72 (s, 3H), 6.84 (m, 2H), 7.10 (m, 2H).

Methyl 4-(2-Hydroxyphenyl)butyrate was reacted with diethylphosphoramidous dichloride as described for example 1, to give the corresponding phosphorous amidite. $^{31}$P NMR (toluene): 142 ppm. The resulting phosphorous amidite was treated with 1M HCl as described for example 1, to yield the corresponding phosphorchloridite. $^{31}$P NMR (toluene): 162 ppm. The phosphorochloridite was then reacted with di-o-tolyl 2,2'-dihydroxyl-1,1'-binaphthalene-3,3'-dicarboxylate in the same manner as described for example 1, to yield ligand 6. NMR indicated a mixture. $^{31}$P NMR (toluene): 130.7, 131.2, 131.8; resonances were about the same intensity.

Example 6A

Hydroformylation of 3-Pentenenitrile with Ligand 6/Rhodium bis(carbonyl)acetylacetonate Reaction was run as in example 4A, but with 2.9 equivalents of Ligand 6 to Rh. GC analysis: (mole %) 2-pentenenitrile 2.6%, valeronitrile 10.0%, 3-pentenenitrile 26.3%, 5-formylvaleronitrile 49.6%. Conversion of pentenenitriles: 74%; selectivity to 5-formylvaleronitrile: 68% on a mole basis; linearity of aldehydes produced: 82%.

Example 6B

Hydroformylation of Methyl 3-pentenoate with Ligand 6/Rhodium bis(carbonyl)acetylacetonate Reaction was run as in example 1B, but with 4.6 equivalents of Ligand 6 to Rh. GC analysis: (mole %) methyl 2-pentenoate 4.6%, methyl valerate 1.7%, methyl-3-pentenoate 49.5%, methyl 5-formylvalerate 41.8%. Conversion of methyl pentenoates: 49%; selectivity to methyl 5-formylvalerate: 85% on a mole basis; linearity of aldehydes produced: 98%.

Example 6C

Hydroformylation of Undecene with Ligand 6/Rhodium bis(carbonyl)acetylacetonate In a drybox was prepared a solution containing undecene (0.5 M), rhodium bis(carbonyl)acetylacetonate (0.85 mM), and 1,2-dichlorobenzene (internal standard, 0.14 M) in toluene. A portion of this solution was added to a glass-lined pressure vessel and enough of a solution of the ligand (0.05 M) in toluene was added to give 5.5 equivalents of Ligand 6 to Rh. The reactor was sealed, pressurized to 0.45 MPa with a 1:1 mixture of CO and H$_2$ and heated to 95° C. for 3 hours. The reactor was cooled and depressurized, and a sample of the reaction mixture was analyzed by gas chromatography on an HP 5890A Gas Chromatograph with a DB-Wax fused silica capillary column (30 meters, 0.32 mm I.D., 0.25 um film thickness) purchased from J&W Scientific Company. GC analysis: (mole %) undecane (1.8%), 1-undecene (3.7%), internal undecenes (52.8%), methylundecanal (0.2%), dodecanal (41.4%). Conversion of undecenes: 58%; selectivity to dodecanal: 97% on a mole basis; linearity of aldehydes produced: 99.5%.

Example 7

Synthesis of Ligand 7

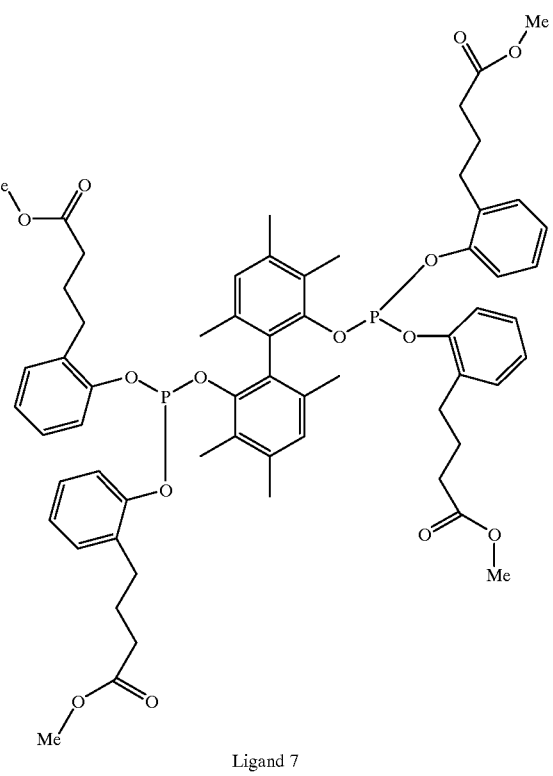

Ligand 7

Methyl 4-(2-Hydroxyphenyl)butyrate was converted to the corresponding phosphorochloridite as described for example 6. The phosphochloridite was reacted with 3,3', 4,4', 6,6'-hexamethyl-2,2'-biphenol, following the procedure described for example 1, to give ligand 7. NMR indicated a mixture. $^{31}$P NMR (toluene): 131, 136, 137; resonances were about the same intensity.

Example 7A

Hydroformylation of 3-Pentenenitrile with Ligand 7/Rhodium bis(carbonyl)acetylacetonate Reaction was run as in example 4A, but with 5.7 equivalents of Ligand 7 to Rh. GC analysis: (mole %) 2-pentenenitrile 2.2%, valeronitrile 10.0%, 3-pentenenitrile 35.4%, 5-formylvaleronitrile 36.6%. Conversion of pentenenitriles: 64%; selectivity to 5-formylvaleronitrile: 57% on a mole basis; linearity of aldehydes produced: 70%.

Example 7B

Hydroformylation of Methyl 3-pentenoate with Ligand 7/Rhodium bis(carbonyl)acetylacetonate Reaction was run as in example 1B, but with 4.6 equivalents of Ligand 7 to Rh. Conversion of methyl pentenoates: 65%; selectivity to methyl 5-formylvalerate: 65% on a mole basis; linearity of aldehydes produced: 93%.

Example 8

Synthesis of Ligand 8

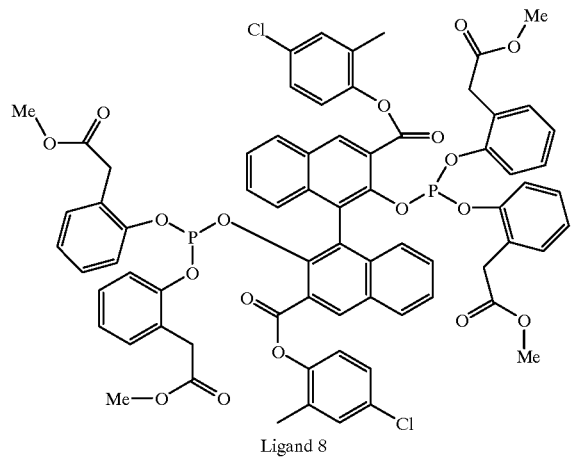

Ligand 8

Methyl 2-hydroxyphenyl acetate was reacted with diethylphosphoramidous dichloride as described in example 1, to yield the corresponding phosphorous amidite. $^{31}$P NMR (toluene): 137 ppm. The phosphorous amidite was treated with 1M HCl solution as described in example 1, to yield the corresponding phosphorochloridite. $^{31}$P NMR (toluene): 158 ppm. The chloridite was then reacted with bis(4-chloro-2-methylphenyl)-2,2'-dihydroxyl-1,1'-binaphthalene-3,3'-dicarboxylate as described in example 1, to yield Ligand 8. $^{31}$P NMR (toluene): 127 (major), 128, 131.

Example 8A

Hydroformylation of 3-Pentenenitrile with Ligand 8/Rhodium bis(carbonyl)acetylacetonate Reaction was run as in example 4A, but with 5.5 equivalents of Ligand 8 to Rh. GC analysis: (mole %) 2-pentenenitrile 2.3%, valeronitrile 8.1%, 3-pentenenitrile 13.5%, 5-formylvaleronitrile 69.8%. Conversion of pentenenitriles: 86%; selectivity to 5-formylvaleronitrile: 81% on a mole basis; linearity of aldehydes produced: 92%.

Example 9

Synthesis of Ligand 9

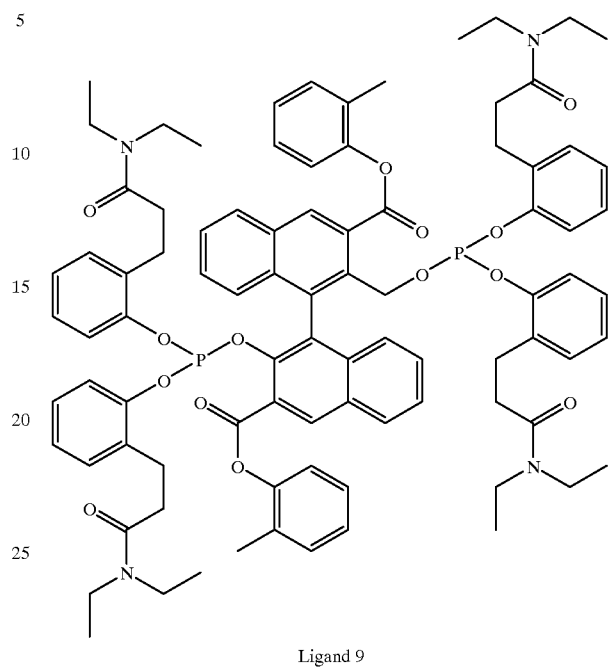

Ligand 9

Diethylamine (98.5 g) and dihydrocoumarin (20.0 g) were refluxed for 4 hours. Excess diethylamine was removed in vacuo to leave 34.0 g of N,N-diethyl-3-(2-hydroxyphenyl) propionamide. $^1$H NMR (CDCl$_3$): 7.26–7.03 (m, 2H), 6.91 (dd, 1H), 6.81 (td, 1H), 3.37 (quartet, 2H), 3.26 (quartet, 2H), 2.95 (m, 2H), 2.71 (m, 2H), 1.10 (quartet, 6H).

In a nitrogen purged glove box, N,N-diethyl-3-(2-hydroxyphenyl) propionamide (5.0 g) was dissolved in 110 mL anhydrous THF (tetrahydrofuran), and cooled to –30° C. To this was added diethylphosphoramidous dichloride (1.97 g), followed by dropwise addition of triethyamine (2.97 g). The mixture was stirred at room temperature for 10 minutes, then kept at –30° C. for 2 hours. The resulting white slurry was filtered over a pad of Celite®, concentrated to yield 6.1 g of the corresponding phosphorous amidite. $^{31}$P NMR (toluene): 141.5 ppm. The above phosphorous amidite (2.5 g) was dissolved in 55 mL anhydrous ether and cooled to –40° C. To the stirring amidite solution was added 11 mL of pre-cooled 1M HCl solution in ether via an addition funnel. Upon addition, white precipitate formed. The mixture was stirred for 10 minutes, and cooled back to –40° C. for 1 hours. The resulting slurry was filtered over a pad of Celite®, and concentrated in vacuo to yield 3.1 g of the corresponding phosphorochloridite. $^{31}$P NMR (toluene): 157.9 ppm. The chloridite was then reacted with di-o-tolyl 2,2'-dihydroxyl-1,1-binaphthalene-3,3'-dicarboxylate as described in example 1, to yield Ligand 9. $^{31}$P NMR (toluene): 132 (major), 134 (minor), 148 (minor).

Example 9A

Hydroformylation of 3-Pentenenitrile with Ligand 9/Rhodium bis(carbonyl)acetylacetonate Reaction was run as in example 4A, but with 10 equivalents of Ligand 9 to Rh. GC analysis: (mole %) 2-pentenenitrile 1.2%, valeronitrile 7.9%, 3-pentenenitrile 21.3%, 5-formylvaleronitrile 57.4%. Conversion of pentenenitriles: 76%; selectivity to 5-formylvaleronitrile: 75% on a mole basis; linearity of aldehydes produced: 86%.

Example 10

Synthesis of Ligand 10

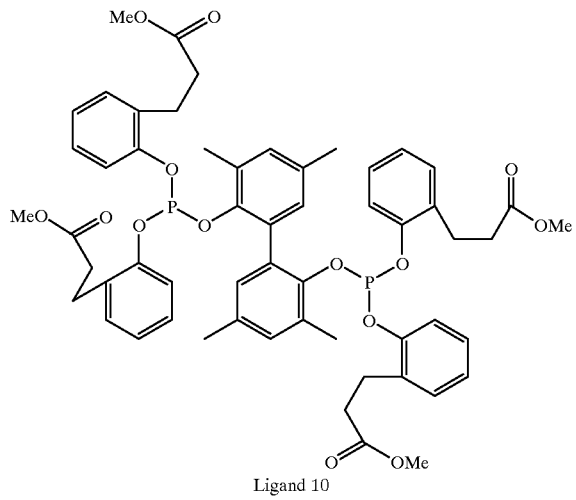

Ligand 10

The procedure of example 2 was followed, except 3,3',5,5'-tetramethyl-2,2'-biphenol was used instead of dimethyl 2,2'-dihydroxyl-1,1'-binaphthalene-3,3'-dicarboxylate. $^{31}$P{H} NMR(202.4 MHz, CDCl$_3$): major resonance at 133.4 ppm with minor resonances at 141.9, 133.6, 130.6 ppm.

Example 10A

Hydroformylation of Methyl 3-Pentenoate with Ligand 10/Rhodium bis(carbonyl)acetylacetonate Reaction was run as in example 1B, but with 4.6 equivalents of Ligand 10 to Rh. GC analysis: (mole %) methyl 2-pentenoate 6.8%, methyl valerate 3.3%, methyl 3-pentenoate 44.4%, methyl 5-formylvalerate 42.4%. Conversion of methyl pentenoates: 55%; selectivity to methyl 5-formylvalerate: 78% on a mole basis; linearity of aldehydes produced: 95%.

Example 11

Synthesis of Ligand 11

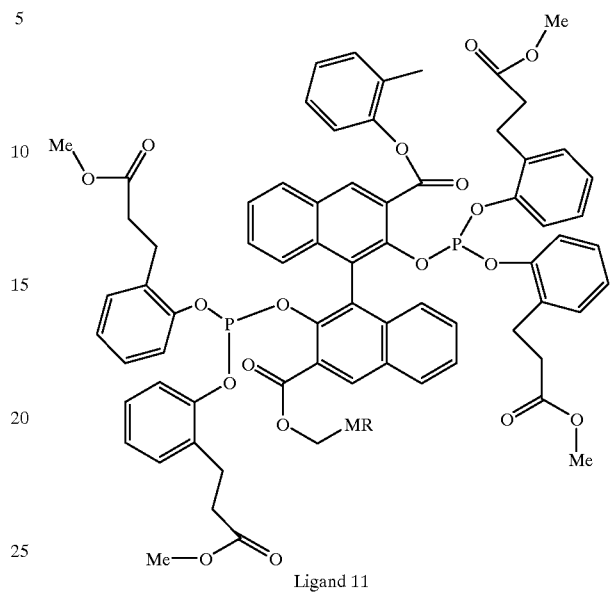

Ligand 11

"MR" denotes Merrifield's resin. 0.757 g (0.6 mmol) of the polymer supported diol prepared by partial esterification of 2,2'-dihydroxyl-1,1'-binapthalene-3,3'-dicarboxylic acid with Merrifield's resin, followed by esterification with o-cresol, was placed in 15 mL of anhydrous toluene, followed by 0.983 g of ClP[OC$_6$H$_4$-2-(CH$_2$)$_2$CO$_2$CH$_3$]$_2$ (2.4 mmol) and 0.465 g of diisopropylethylamine (3.6 mmol). After shaking overnight, the resin changed from orange to light yellow. The supported ligand was collected by filtration and washed with toluene (20 mL), tetrahydrofuran (20 mL), and CH$_2$Cl$_2$ (20 mL) before drying under vacuum; Elemental analysis: 1.74–1.97 wt % P; IR (KBr): 1736 cm$^{-1}$ (vs).

A portion of the supported ligand was treated with excess Ni(COD)$_2$, followed by about 0.1 MPa of carbon monoxide to give the supported complex P$_2$Ni(CO)$_2$ (P$_2$ denotes the supported ligand). The infrared spectrum of this material shows, in addition to an ester band at 1730 cm$^{-1}$, strong bands at 2045 and 1996 cm$^{-1}$, consistent with formation of the desired dicarbonyl species. A very weak band at 2084 cm$^{-1}$ indicates formation of a trace amount of a supported PNi(CO)$_3$ species, where P denotes a supported monophosphite ligand.

Example 11A

Hydroformylation of 3-Pentenenitrile with Ligand 11/Rhodium bis(carbonyl)acetylacetonate In a drybox was prepared a solution containing 3-pentenenitrile (0.5 M), rhodium bis(carbonyl) acetylacetonate (0.85 mM), and 1,2-dichlorobenzene (internal standard, 0.14 M) in toluene. A portion of this solution was added to a glass-lined pressure vessel containing 5.3 molar equivalents of Ligand 11 to Rh. The reactor was sealed, pressurized to between 0.45 MPa with a 1:1 mixture of CO and H$_2$ and heated to between 95° C. for 3 hours. The reactor was cooled and depressurized, and a sample of the reaction mixture was analyzed by gas chromatography on an HP 5890A Chromatograph with a Quadrex 23 fused silica capillary column (30 meters, 0.32 mm I.D., 0.25 um film thickness) purchased from the Quadrex Corporation. GC analysis: GC analysis: (mole %) 2-pentenenitrile 4.7%, valeronitrile 13.6%, 3-pentenenitrile 23.3%, 5-formylvaleronitrile 46.3%. Conversion of pentenenitriles: 77%; selectivity to 5-formylvaleronitrile: 60% on a mole basis; linearity of aldehydes produced: 79%.

Example 11B

Hydroformylation of Methyl 3-Pentenoate with Ligand 11/Rhodium bis(carbonyl)acetylacetonate 5 In a drybox was prepared a solution containing methyl-3-pentenoate (0.5 M), rhodium bis(carbonyl)acetylacetonate (1.0 mM), and 1,2-dichlorobenzene (internal standard, 0.14 M) in toluene. A portion of this solution was added to a glass-lined pressure vessel containing 4.9 molar equivalents of Ligand 11 to Rh. The reactor was sealed, pressurized to 0.45 MPa with a 1:1 mixture of CO and $H_2$ and heated to 95° C. for 3 hours. The reactor was cooled and depressurized, and a sample of the reaction mixture was analyzed by gas chromatography on an HP 5890A Chromatograph with a DB-FFAP fused silica capillary column (30 meters, 0.32 mm I.D., 0.25 um film thickness) purchased from JW Scientific. GC analysis: (mole %) methyl-2-pentenoate 2.7%, methyl valerate 0.8%, methyl-3-pentenoate 75.3%, methyl 5-formylvalerate 19.1%. Conversion of methyl pentenoates: 24%; selectivity to methyl 5-formylvalerate: 79% on a mole basis; linearity of aldehydes produced: 93%.

Examples 12, 13, 14

Synthesis of Ligands 12, 13, and 14

Ligands 12, 13, and 14 were prepared as described for Ligand 11 in example 11. Characterization data is provided in Table 1. "MR" in the structures below refers to Merrifield's resin.

TABLE 1

Characterization Data for polymer-bound ligands

| Example | Ligand | Structure | Elemental Analysis (wt % P) | IR (KBr, cm[1]) |
|---|---|---|---|---|
| 12 | 12 | 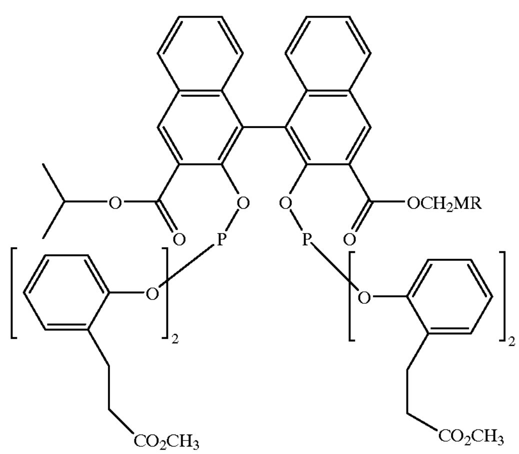 | 2.03 | 1736 (vs) |
| 13 | 13 | 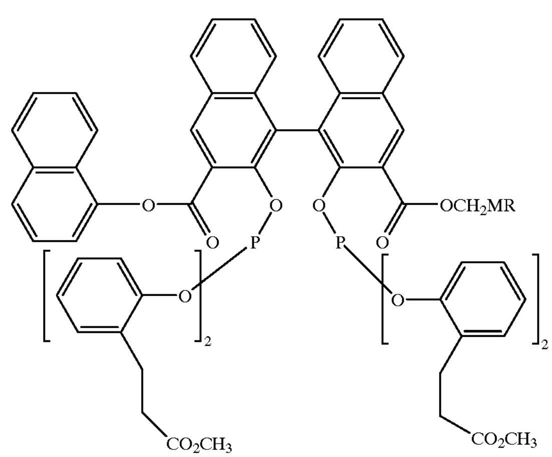 | 1.76 | 1734 (vs) |

TABLE 1-continued

Characterization Data for polymer-bound ligands

| Example | Ligand | Structure | Elemental Analysis (wt % P) | IR (KBr, cm⁻¹) |
|---------|--------|-----------|------------------------------|----------------|
| 14 | 14 | (structure shown) | 1.80 | 1734 (vs) |

Examples 12A–14A

Reactions were run as in example 11A. The results are summarized in Table 2, in which "CONV" (conversion) is the percentage of 3 and 4 pentenenitrile which is converted to products, "SEL" (selectivity) is the percentage of the product mixture that is comprised of 5-formylvaleronitrile, and "LIN" (linearity) is the percentage the aldehyde products that is comprised of 5-formylvaleronitrile.

TABLE 2

3-Pentenenitrile Hydroformylation Results for polymer-bound ligands

| Example | Ligand | CONV | SEL | LIN |
|---------|--------|------|------|------|
| 12A | 12 | 65.5 | 64.2 | 77.3 |
| 13A | 13 | 64.7 | 59.2 | 71.9 |
| 14A | 14 | 86.7 | 57.6 | 73.8 |

Examples 12B–14B

The ligands were prepared as above. Reactions using methyl 3-pentenoate as reactant were run as in Example 11B. Results are in Table 3.

TABLE 3

Methyl 3-Pentenoate Hydroformylation Results

| Example | Ligand | CONV | SEL | LIN |
|---------|--------|------|------|------|
| 12B | 12 | 54.8 | 81.2 | 93.3 |
| 13B | 13 | 68.9 | 82.5 | 93.4 |
| 14B | 14 | 55.4 | 80.3 | 92.0 |

Comparative Example 1

Synthesis of Ligand 15

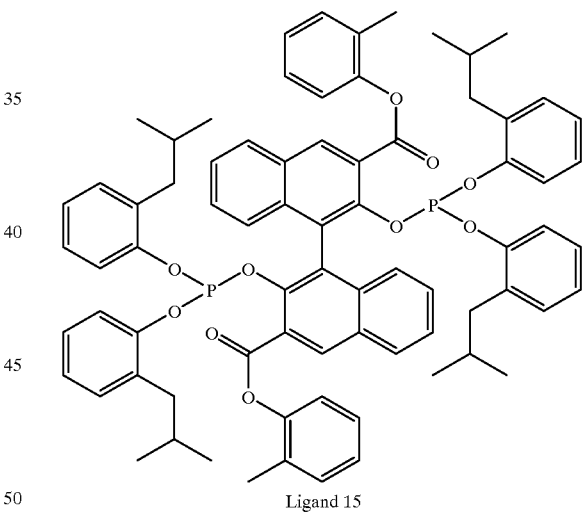

Ligand 15

2-Hydroxy-isobutyrophenone was prepared from phenol following the procedure described in *Canadian Journal of Chemistry*, 31, 1956, 851. To a solution of 2-hydroxy-isobutyrophenone (2g, 12.2 mmol) in trifluroacetic acid (14 g, 122 mmol) was slowly added triethylsilane (26.8 mmol). The solution was stirred at room temperature for 6 hours. Saturated sodium bicarbonate solution was added to the reaction mixture, followed by ether. The layers were separated, and the aqueous layer was extracted with ether. The organic layers were combined, dried over magnesium sulfate, and concentrated. The crude material was distilled under vacuum (about $9.3 \times 10^{-4}$ MPa, 75° C.). The distillate was washed with potassium hydroxide solution, followed by addition of hydrogen chloride solution, and extraction with ether. The ether layers were combined, dried over magnesium sulfate, and concentrated to give 1.0 g (55%) of 2-isobutylphenol. $^1$H NMR (300 Mhz, δ, CDCl$_3$): 7.0 (m, 2H), 6.8 (t, 1H), 6.7 (d, 1H), 4.6 (br. s, 1H), 2.4 (d, 2H), 1.9 (s, 1H), 0.9 (d, 6H).

The above phenol (0.78 g) was dissolved in 25 mL diethyl ether, and cooled to −40° C. in a nitrogen purged glove box. Triethylamine (0.68 g) was added, followed by the addition of 0.45 g of diethylphosphoramidous dichloride. Upon addition of diethylphosphoramidous dichloride, a white precipitate formed. The reaction mixture was stirred at room temperature for one hour, then filtered over a pad of Celite®. The filtrate was concentrated in vacuo to yield 1.0 g (97%) of the corresponding phorphorous amidite. $^{31}$P NMR (toluene): 136 ppm. The above phosphorous amidite (1.0 g) was dissolved in 25 mL anhydrous ether and cooled to −40° C. To the stirring amidite solution was slowly added 5.0 mL of pre-cooled 1M HCl solution in ether. Upon addition, white precipitate formed. The mixture was stirred for 10 minutes, and cooled back to −40° C. for 2 hours. The resulting slurry was filtered over a pad of Celite®, and concentrated in vacuo to yield 0.85 g of the corresponding phosphorochloridite. $^{31}$P NMR (toluene): 161 ppm.

The above phosphorochloridite was reacted with di-o-tolyl 2,2'-dihydroxyl-1,1'-binaphthalene-3,3'-dicarboxylate and triethylamine in the same manner as described for example 1 to yield Ligand 15. $^{31}$P NMR (toluene): 129.9 ppm.

Comparative Example 1A

Hydroformylation of 3-Pentenenitrile with Ligand 15/Rhodium bis(carbonyl)acetylacetonate Reaction was run as in example 4A, but with Ligand 15. Conversion of 3-pentenenitrile: 73%; selectivity to 5-formylvaleronitrile: 64% on a mole basis; linearity of aldehydes produced: 73%.

Comparative Example 1B

Hydroformylation of Methyl 3-Pentenoate with Ligand 15/Rhodium bis(carbonyl)acetylacetonate Reaction was run as in example 1B, but with 4.6 equivalents of Ligand 15 to Rh. GC analysis: (mole %) methyl 2-pentenoate 5.5%, methyl valerate 1.5%, methyl 3-pentenoate 46.7%, methyl 5-formylvalerate 43.3%. Conversion of pentenenitriles: 83%; selectivity to methyl 5-formylvalerate: 78% on a mole basis; linearity of aldehydes produced: 96%.

In contrast to the prior art, multidentate phosphite ligands of the present invention in which at least one $R^1$ group is $R^3Z$ provide high selectivities in the hydroformylation of 3-pentenenitrile. A comparison of the performance of comparative example Ligand 15 with that of sterically similar Ligand 1 (a ligand of the present invention) shows that the selectivity in 3-pentenenitrile hydroformylation is 14% higher for Ligand 1. Similarly, Ligand 1 performed better in methyl-3-pentenoate hydroformylation than the sterically analogous comparative example Ligand 15, leading to 10% higher selectivity of 5-formylvalerate.

What is claimed is:

1. A multidentate phosphite ligand of the formulae I, II or III:

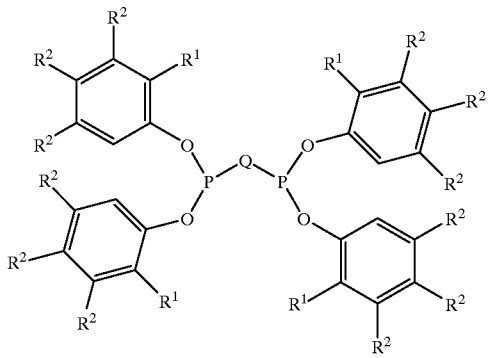

I

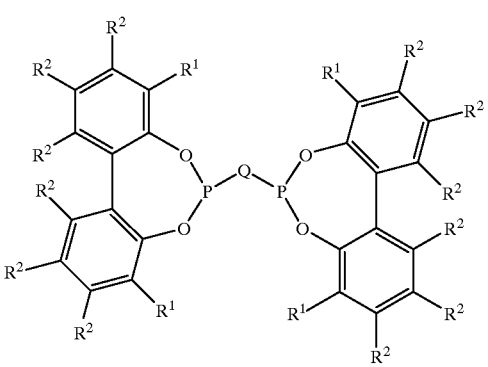

II

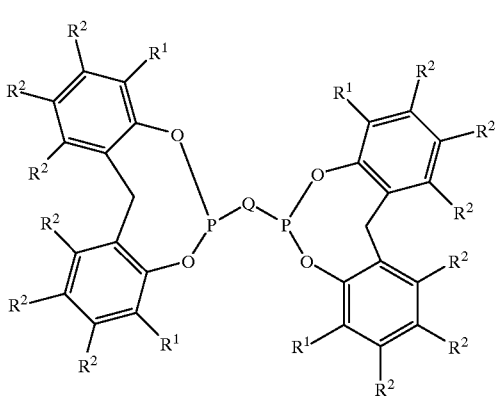

III wherein:
each $R^1$ independently is $C_1$ to $C_{12}$ alkyl, $C_6$ to $C_{20}$ aryl, F, Cl, —$CO_2R^4$, —$OR^4$, or —$R^3Z$, provided that at least one $R^1$ is —$R^3Z$;
each $R^2$ independently is H, F, Cl, $C_1$ to $C_{12}$ alkyl, $C_6$ to $C_{20}$ aryl, —$OR^4$, —$CO_2R^4$, —$C(O)R^4$, —CHO, —CN, or —$CF_3$;
each $R^3$ independently is $C_1$ to $C_{10}$ alkylene;
each $R^4$ independently is $C_1$ to $C_{12}$ alkyl or $C_6$ to $C_{20}$ aryl;
each Z is —$CO_2R^4$, —CHO, —$C(O)R^4$, —$C(O)SR^4$, —$SR^4$, —$C(O)NR^5R^6$, —$OC(O)R^4$, —$OC(O)OR^4$, —N=CR$^5$R$^6$, —C(R$^5$)=NR$^6$, —C(R$^5$)=N—O—R$^6$, —P(O)(OR$^4$)(OR$^4$), —S(O)$_2$R$^4$, —S(O)R$^4$, —C(O)OC(O)R$^4$, —NR$^4$CO$_2$R$^4$, —NR$^4$C(O)NR$^5$R$^6$, or —CN;

each R$^4$ independently is C$_1$ to C$_{12}$ alkyl or C$_6$ to C$_{20}$ aryl;

each R$^5$ independently is H, C$_1$ to C$_{12}$ alkyl, or C$_6$ to C$_{20}$ aryl;

each R$^6$ independently is H, C$_1$ to C$_{12}$ alkyl, or C$_6$ to C$_{20}$ aryl;

Q is a divalent bridging group of the formula:

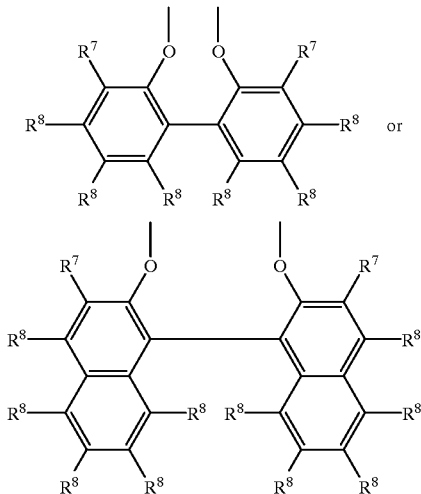

wherein:
each R$^7$ independently is H, F, Cl, C$_1$ to C$_{12}$ alkyl, C$_6$ to C$_{20}$ aryl, —OR$^4$, —CO$_2$R$^4$, —C(O)R$^4$, —C(R$^5$)=N—O—R$^6$, —CHO, —CN, —CF$_3$, —C(R$^5$)=NR$^6$, —NR$^5$R$^6$ or —R$^3$Z; and each R$^8$ is H, F, Cl, C$_1$ to C$_{12}$ alkyl, C$_6$ to C$_{20}$ aryl, —OR$^4$, —CO$_2$R$^4$, —C(O)R$^4$, —CN, or —CF$_3$.

2. The multidentate phosphite ligand of claim 1 in which the ligand is of formula I wherein:
each R$^1$ independently is —R$^3$Z;
each R$^2$ independently is H, F, Cl, C$_1$ to C$_{12}$ alkyl, C$_6$ to C$_{20}$ aryl, —OR$^4$, —CO$_2$R$^4$, —C(O)R$^4$, —CHO, —CN, or —CF$_3$;
each R$^3$ independently is C$_1$ to C$_4$ alkylene;
each Z independently is —CO$_2$R$^4$, —CHO, —C(O)R$^4$, —C(O)NR$^5$R$^6$, —OC(O)R$^4$, —OC(O)R$^4$, —N=CR$^5$R$^6$, or —C(R$^5$)=NR$^6$ Q is a divalent bridging group of the formula:

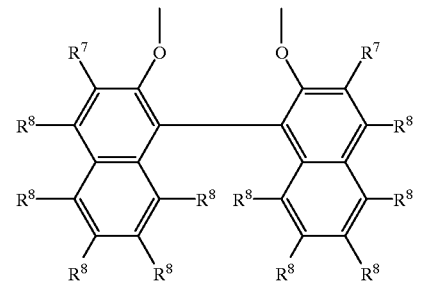

wherein:
each R$^7$ independently is —CO$_2$R$^4$, —C(O)R$^4$, —C(R$^5$)=N—O—R$^6$, —CHO, —CN, or —C(R$^5$)=N(R$^6$); and each R$^8$ independently is H, F, Cl, C$_1$ to C$_{12}$ alkyl, C$_6$ to C$_{20}$ aryl, OR$^4$, —CO$_2$R$^4$, —C(O)R$^4$, —CN, or —CF$_3$.

3. The multidentate phosphite ligand of claim 2 in which each R$^2$ is H; each R$^3$ is C$_1$ to C$_3$ alkylene; each Z is —CO$_2$R$^4$.

4. A catalyst comprising a Group VIII transition metal and a multidentate phosphite ligand selected from the group represented by the formulae I, II or III:

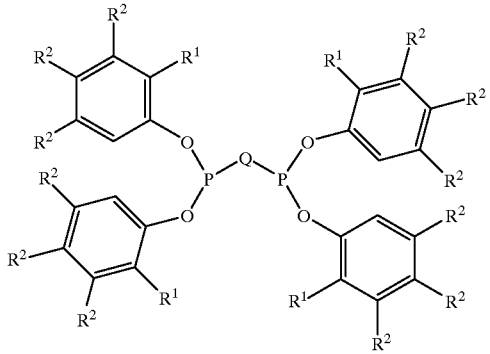

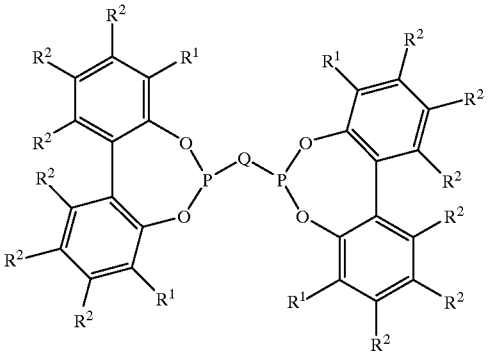

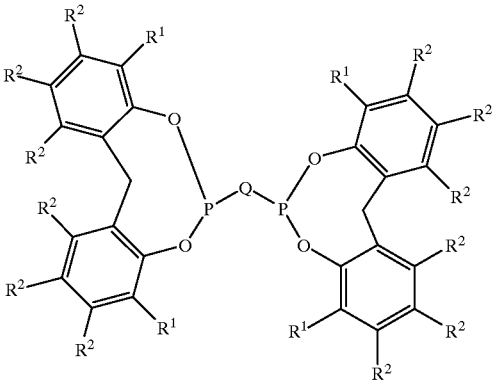

wherein:
each R$^1$ independently is C$_1$ to C$_{12}$ alkyl, C$_6$ to C$_{20}$ aryl, F, Cl, —CO$_2$R$^4$, —OR$^4$, or —R$^3$Z, provided that at least one R$^1$ is —R$^3$Z;

each $R^2$ independently is H, F, Cl, $C_1$ to $C_{12}$ alkyl, $C_6$ to $C_{20}$ aryl, —$OR^4$, —$CO_2R^4$, —$C(O)R^4$, —CHO, —CN, or —$CF_3$;

each $R^3$ independently is $C_1$ to $C_{10}$ alkylene;

each $R^4$ independently is $C_1$ to $C_{12}$ alkyl or $C_6$ to $C_{20}$ aryl;

each Z is —$CO_2R^4$, —CHO, —$C(O)R^4$, —$C(O)SR^4$, —$SR^4$, —$C(O)NR^5R^6$, —$OC(O)R^4$, —$OC(O)OR^4$, —$N=CR^5R^6$, —$C(R^5)=NR^6$, —$C(R^5)=N-O-R^6$, —$P(O)(OR^4)(OR^4)$, —$S(O)_2R^4$, —$S(O)R^4$, —$C(O)OC(O)R^4$, —$NR^4CO_2R^4$, —$NR^4C(O)NR^5R^6$, or —CN;

each $R^4$ independently is $C_1$ to $C_{12}$ alkyl or $C_6$ to $C_{20}$ aryl;

each $R^5$ independently is H, $C_1$ to $C_{12}$ alkyl, or $C_6$ to $C_{20}$ aryl;

each $R^6$ independently is H, $C_1$ to $C_{12}$ alkyl, or $C_6$ to $C_{20}$ aryl;

Q is a divalent bridging group of the formula:

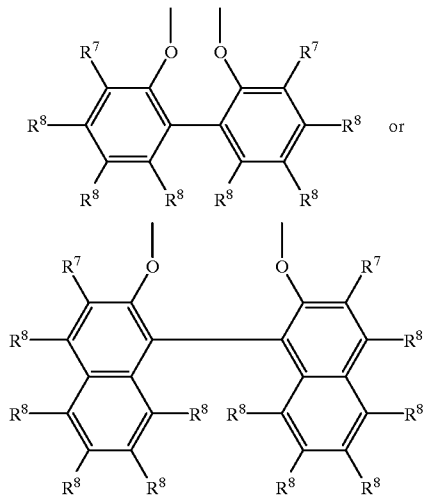 or wherein:
each $R^7$ independently is H, F, Cl, $C_1$ to $C_{12}$ alkyl, $C_6$ to $C_{20}$ aryl, —$OR^4$, —$CO_2R^4$, —$C(O)R^4$, —$C(R^5)=N-O-R^6$, —CHO, —CN, —$CF_3$, —$C(R^5)=NR^5$, —$NR^5R^6$ or —$R^3Z$; and each $R^8$ is H, F, Cl, $C_1$ to $C_{12}$ alkyl, $C_6$ to $C_{20}$ aryl, —$OR^4$, —$CO_2R^4$, —$C(O)R^4$, —CN, or $CF_3$.

5. The catalyst composition of claim 4 in which the ligand is of formula I wherein:

each $R^1$ independently is —$R^3Z$;

each $R^2$ independently is H, F, Cl, $C_1$ to $C_{12}$ alkyl, $C_6$ to $C_{20}$ aryl, —$OR^4$, —$CO_2R^4$, —$C(O)R^4$, —CHO, —CN, or —$CF_3$;

each $R^3$ independently is $C_1$ to $C_4$ alkylene;

each Z independently is —$CO_2R^4$, —CHO, —$C(O)R^4$, —$C(O)NR^5R^6$, —$OC(O)R^4$, —$OC(O)OR^4$, —$N=CR^5R^6$, or —$C(R^5)=NR^6$;

Q is a divalent bridging group of the formula:

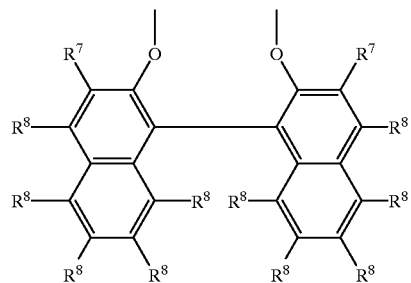

wherein:
each $R^7$ independently is —$CO_2R^4$, —$C(O)R^4$, —$C(R^5)=N-O-R^6$, —CHO, —CN, or —$C(R^5)=N(R^6)$; and each $R^8$ independently is H, F, Cl, $C_1$ to $C_{12}$ alkyl, $C_6$ to $C_{20}$ aryl, $OR^4$, —$CO_2R^4$, —$C(O)R^4$, —CN, or —$CF_3$.

6. The catalyst composition of claim 5 in which each $R^2$ is H; each $R^3$ is $C_1$ to $C_3$ alkylene; each Z is —$CO_2R^4$.

7. The catalyst composition of claim 6 in which the metal is selected from the group consisting of rhodium, cobalt, iridium, palladium, and platinum.

8. The catalyst composition of claim 7 in which the metal is rhodium.

9. The catalyst composition of claim 8 in which the rhodium is in the form of a rhodium hydride, halide, organic acid salt, acetylacetonate, inorganic acid salt, oxide, carbonyl compound, or amine compound.

10. The catalyst composition of claim 9 in which the rhodium is in the form of rhodium bis(carbonyl) acetylacetonate.

* * * * *